(12) United States Patent
Peng et al.

(10) Patent No.: US 10,543,367 B2
(45) Date of Patent: Jan. 28, 2020

(54) TRANSCRANIAL BURST ELECTROSTIMULATION APPARATUS AND ITS APPLICATIONS

(71) Applicants: TAIPEI MEDICAL UNIVERSITY, Taipei (TW); NATIONAL APPLIED RESEARCH LABORATORIES, Taipei (TW)

(72) Inventors: Chih-Wei Peng, Taipei (TW); Shih-Ching Chen, Taipei (TW); Yu Ting Li, Taipei (TW); Hsiang Ching Lee, Taipei (TW); Jia-Jin J. Chen, Taipei (TW); Tsung-Hsun Hsieh, Taipei (TW); Chien-Hung Lai, Taipei (TW); Jiunn-Horng Kang, Taipei (TW)

(73) Assignees: TAIPEI MEDICAL UNIVERSITY, Taipei (TW); NATIONAL APPLIED RESEARCH LABORATORIES, Taipei (TW)

(*) Notice: Subject to any disclaimer, the term of this patent is extended or adjusted under 35 U.S.C. 154(b) by 98 days.

(21) Appl. No.: 14/743,183

(22) Filed: Jun. 18, 2015

(65) Prior Publication Data
US 2016/0367804 A1 Dec. 22, 2016

(51) Int. Cl.
*A61N 1/36* (2006.01)
*A61N 1/04* (2006.01)
*A61N 1/20* (2006.01)

(52) U.S. Cl.
CPC ....... *A61N 1/36025* (2013.01); *A61N 1/0456* (2013.01); *A61N 1/0472* (2013.01); *A61N 1/20* (2013.01)

(58) Field of Classification Search
None
See application file for complete search history.

(56) References Cited

U.S. PATENT DOCUMENTS

| 2006/0015153 A1* | 1/2006 | Gliner | A61N 1/3606 607/45 |
| 2014/0058189 A1* | 2/2014 | Stubbeman | A61N 2/002 600/13 |
| 2015/0328467 A1* | 11/2015 | Demers | A61N 1/36014 607/45 |

* cited by examiner

*Primary Examiner* — Erica S Lee
(74) *Attorney, Agent, or Firm* — WPAT, P.C., Intellectual Property Attorneys; Anthony King

(57) ABSTRACT

The invention provides transcranial electrostimulation by combining transcranial direct current stimulation (tDCS) and theta burst stimulation (TBS) to achieve an unexpected therapeutic effect in various brain or neural diseases. Accordingly, the invention provides a mode of direct current with biphasic square wave pulses in the treatment of brain or neural diseases. Also provided are methods of employing the transcranial electrostimulation of the invention and applications of the transcranial electrostimulation of the invention.

13 Claims, 6 Drawing Sheets

TRANSCRANIAL BURST ELECTROSTIMULATION APPARATUS AND ITS APPLICATIONS

FIELD OF THE INVENTION

The invention relates to a transcranial electrostimulation system. More, particularly, the invention relates to a transcranial electrostimulation system using direct current in combination with biphasic square wave pulses.

BACKGROUND OF THE INVENTION

Traumatic brain injuries can result in physical and emotional dysfunction. Given the prevalence of age-related cognitive decline conditions, injury from a fall, cerebral-vascular events, neurodegenerative conditions (i.e., Alzheimer's Disease) and the many brain injuries occurring in sports and in military operation theaters, there is a need to develop a therapy for these diseases. Therapeutic stimulation modalities have had a key role in development of treatment for a number of neuropsychiatric disorders. Stimulation of tissue in humans and other animals is used in a number of clinical applications as well as in clinical and general biological research. In particular, stimulation of neural tissue has been used in the treatment of various diseases, including Parkinson's disease, depression, and intractable pain. The stimulation may be applied invasively, e.g., by performing surgery to remove a portion of the skull and implanting electrodes in a specific location within brain tissue, or non-invasively, e.g., transcranial direct current stimulation and transcranial magnetic stimulation.

There are two types of noninvasive brain stimulation techniques in the research literature, transcranial magnetic stimulation and transcranial direct current stimulation. There are subcategories within these two types of stimulation. TMS can be delivered as a continuous wave of stimulation, pulsed (repetitive or rTMS), or as a burst (theta-burst TMS). The other method uses electrical rather than magnetic stimulation and can be delivered through transcranial direct current (tDCS) or pulsed current (tPCS).

Direct current stimulation has been shown to be well tolerated in applications to the brain through the skull or cranium. It is described as transcranial direct current stimulation and is accomplished by multiple devices that generate continuous low current ion flow through the skull into the brain tissue. Other forms of brain stimulation involve creating holes in the skull and implanting a variety of energy transmitters.

Transcranial current stimulation (TCS) is a neuromodulation method in which the patient is exposed to a mild electric current (direct or alternating) at 1-2 mA, resulting in an increase or decrease in brain excitability. Considerable methodological details on using TCS in basic and clinical neuroscience studies in human subjects have been introduced and technical characteristics of TCS devices and their related accessories with regard to safety concerns have also been well articulated (C. Rossi et al., European Journal of Neurology 2013, 20: 202-204; Maryam Rostami et al., Basic and Clinical Neuroscience, 2013, Vol. 4, No. 3, pp. 8-26).

US20090319002 A1 relates to systems, apparatus and methods for applying electric current to neurons in the brain to treat disorders and to improve motor and/or memory functions in a patient, wherein an electrode is positioned adjacent to and spaced from the skin surface of the patient's head and an electric current is applied through the electrode to a target region in the brain to modulate one or more neurons in the target region. US20130281759 A1 provides a joint brain electro-analysis and transcranial current stimulation system comprising a plurality of spaced-apart removable and replaceable electrodes arranged in a piece of headgear, an electroencephalography device wired to each of the electrodes, and a transcranial current stimulation device wired to each of the electrodes. US20140018881 A1 provides a device for transcranial stimulation comprising an alternating current source for providing a stimulation current; a first electrode connected to the current source for electrical connection to a patient; a second electrode connected to the current source for electrical connection to the patient; a first current interrupter for interrupting current flow between the current source and the electrode, the first current interrupter connected between the alternating current source and the first electrode; and an output monitor connected between the current source and the first electrode for monitoring current to the patient.

Lindsay Oberman et al. highlight the need for rigorous documentation of adverse events associated with theta-burst stimulation (TBS), as well intensity dosing studies to assess the seizure risk associated with various stimulation parameters (e.g. frequency, intensity, location) (J Clin Neurophysiol. 2011 February; 28(1): 67-74). Continuous theta-burst stimulation (cTBS) applied over the cerebellum exerts long-lasting effects by modulating long-term synaptic plasticity, which is thought to be the basis of learning and behavioral adaptation.

However, there is a need to develop a transcranial electrostimulation system providing better brain or neuronal plasticity and treatment efficacy.

SUMMARY OF THE INVENTION

The invention provides a transcranial electrostimulation by combining a transcranial direct current stimulation (tDCS) and theta burst stimulation (TBS) and its applications in treatment.

The invention provides a transcranial electrostimulator, comprising an alternating current source for providing direct current stimulation (tDCS) and a theta burst stimulation (TBS). The tDCS is delivered with an adjustable direct current in a range of about 0 to +/− about 10 mA and the TBS is delivered with an alternating current with amplitude ranging from 0 to +/−1.5 mA and multiple bursts each having 2 to 6 pulses, each pulse having a pulse width of about 0.5 to about 2 ms and a gap of about 15 ms to 25 ms and repeating every 150 ms to 250 ms. The bursts are continuous to provide continuous TBS (cTBS) or intermittent to provide intermittent TBS (iTBS). Preferably, the stimulation direct current provided by the transcranial electrostimulator of the invention is about 0 to +/− about 9, 8, 7, 6, 5, 4, 3, 2, or 1 mA; more preferably, about 0 to +/− about 3 mA.

In some embodiments, the multiple bursts of the TBS of the invention include 5 to 20 bursts per stimulation; more preferably 10 bursts. In some embodiments, a burst comprises 2 to 6 pulses (more preferably 3 pulse), each pulse having a pulse width of about 0.5 to about 2 ms (preferably about 1 ms) and a gap of about 15 ms to about 25 ms (more preferably about 20 ms) and repeating at intervals of about 150 ms to about 250 ms (more preferably about 200 ms). In some embodiments, the bursts are continuous to provide continuous TBS (cTBS) or intermittent to provide intermittent TBS (iTBS). In one embodiment, the intermittent period between bursts of the iTBS is about 4 seconds to about 15 seconds, more preferably 8 seconds.

In some embodiments, the TBS is delivered for 0 to 60 minutes, more preferably about 30 minutes. In some embodiments, cTBS or iTBS can optionally include a time delay between bursts. Preferably, the time delay is about 0 seconds to about 20 seconds, preferably 0 seconds to 15 seconds.

The invention also provides a disposable and portable electrode, said electrode comprising a plastic packet having two compartments, one compartment containing a liquid-absorbable pad and the other compartment containing a conductive medium at a predetermined concentration and volume sufficient to provide a desired conductivity, one or more fasteners on one side and one or more corresponding depressed elements on the opposite side of the packet, wherein there is an openable seal line between the two compartments.

The invention also provides a transcranial electrostimulation apparatus, comprising:
 (i) a transcranial electrostimulator of the invention;
 (ii) one or more electrodes of the invention for detachable attachment to the scalp of a subject, the electrode(s) being driven by the transcranial burst electrostimulator; and
 (iii) a flexible head brace for adjustably securing the electrode(s), wherein the electrode(s) can be adjustably positioned anywhere on the head brace.

The invention also further provides a method of applying a transcranial electrostimulation to a subject, comprising:
 (i) providing a transcranial electrostimulator of the invention comprising an alternating current source to provide both direct current stimulation (tDCS) and theta burst stimulation (TBS) as mentioned in the invention;
 (ii) sending an electrostimulation signal to electrodes of the invention; and
 (iii) transferring the electrostimulation signal from the electrodes to the subject.

The transcranial electro stimulation of the invention may facilitate enhanced functional recovery or development in patients experiencing neurologic dysfunction associated with stroke, TBI, learning and/or memory disorders, Alzheimer's disease, and/or other conditions.

DETAILED DESCRIPTION OF THE INVENTION

Figure 1:
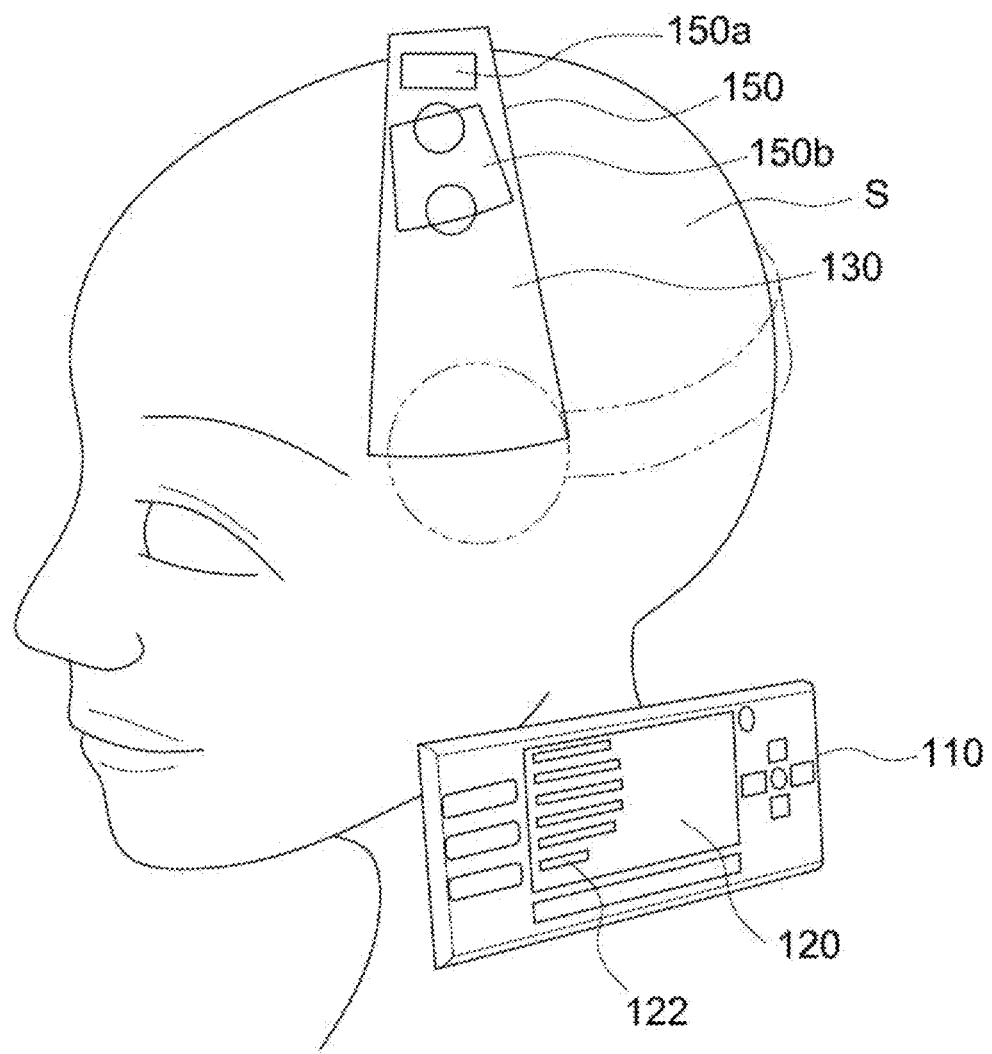
FIG. 1 is a schematic diagram of a system for applying transcranial electrostimulation to a stimulation site or region in accordance with an embodiment of the invention.

The present invention will now be described more fully hereinafter with reference to the accompanying drawings, in which preferred embodiments of the present invention are shown. This invention may however, be embodied in many different forms and should not be construed as limited to the embodiments set forth herein. Rather, these embodiments are provided so that this application will be thorough in illustration to convey the true scope of the invention to those skilled in the art. Some illustrations provided herein include detailed explanations of dimension and operation, which should also not serve as limitations.

The invention provides transcranial electrostimulation by a combination of transcranial direct current stimulation (tDCS) and theta burst stimulation (TBS) delivered in the form of an adjustable current and multiple bursts to achieve an unexpected therapeutic effect in various brain or neural diseases. Accordingly, the invention provides a mode of direct current with biphasic square wave pulses in the treatment of brain or neural diseases.

In one aspect, the invention provides a transcranial electrostimulator, comprising an alternating current source for providing direct current stimulation (tDCS) in combination with theta burst stimulation (TBS); the tDCS is delivered with an adjustable direct current in a range of about 0 to +/− about 5 mA and the TBS is delivered with an alternating current with amplitude ranging from 0 to +/−5 mA and multiple bursts each having 2 to 5 pulses, each pulse having a pulse width of about 0.1 to about 3 ms and a gap of about 5 ms to 30 ms and repeating every 150 ms to 500 ms; the bursts are continuous to provide continuous TBS (cTBS) or intermittent to provide intermittent TBS (iTBS).

In some embodiments, the stimulation direct current provided by the transcranial electrostimulator of the invention is in a predetermined range, i.e., about 0 to +/− about 5 mA; preferably about 0 to +/− about 4, 3, 2, or 1 mA; more preferably about 0 to +/− about 3 mA.

Theta burst stimulation (TBS) is a recently developed painless variant whose high-frequency bursts of short duration and low intensity induce long-term after-effects that outlast the period of stimulation. Two kinds of TBS, intermittent TBS (iTBS) and continuous TBS (cTBS), modulate human cortical excitability differently, with iTBS increasing it and cTBS decreasing it; cTBS is a form of continuous transcranial stimulation, while iTBS is a form of repetitive transcranial stimulation. As used herein, a "burst" of stimulation may include a certain number and kind of pulses, or may be defined as continuous delivery of certain kind of pulses for an indeterminate interval, and a given instance of a stimulation therapy may be defined to include one or more bursts. When multiple bursts are to be delivered for a given stimulation therapy, another parameter may allow a user to program a time delay between bursts (e.g., an interburst interval). In some neurostimulation systems, parameters may be available that allow a user to program a stimulation therapy to be triggered when the neurostimulator detects a pattern or "event" in electrographic signals being monitored from the patient.

In some embodiments, a TBS of the invention may include, but is not limited to, for example, 2 to 30 bursts per stimulation; or preferably 5 to 15 bursts or 8 to 12 bursts, or more preferably 10 bursts. In some embodiments, a burst comprises 2 to 5 pulses (or preferably 2 to 4 pulses, or more preferably 3 pulses), and each pulse has a pulse width of about 0.1 to about 3 ms (or preferably about 1 ms) and there is a gap of about 5 ms to about 30 ms (or preferably about 18 ms to about 22 ms, or more preferably about 20 ms) between every two pulses of a burst. The period of a TBS, e.g. the interval from an initial time of a burst to an initial time of the next burst, is about 150 ms to about 500 ms (or preferably about 180 ms to about 470 ms, or more preferably about 200 ms). In some embodiments, the bursts are continuous to provide continuous TBS (cTBS) or intermittent to provide intermittent TBS (iTBS). In one embodiment, the intermittent period between every two TBSs (or between the last burst of a TBS and the first burst of the next TBS) of the iTBS is about 2 seconds to about 30 seconds, or preferably about 5 seconds to about 27 seconds, or more preferably, 8 seconds.

In some embodiments, the TBS is delivered for more than 0 to 60 minutes, preferably 0 to 45 minutes, or more preferably about 30 minutes.

In some embodiments, there is a time delay prior to the first burst of the TBS. Preferably, the time delay is about 0 seconds to about 20 seconds, preferably, 0 seconds to 15 seconds.

In one aspect, the invention provides a disposable and portable electrode, said electrode comprising a plastic packet having two compartments, one compartment containing a liquid-absorbable pad and the other compartment containing a conductive medium in a predetermined concentration and volume sufficient to provide a desired conductivity, one or more fasteners on one side and one or more corresponding depressed elements on the opposite side of the packet, wherein there is an openable seal line between the two compartments.

In one embodiment, the liquid-absorbable pad is a sponge, water-absorbable polymer or water-absorbable texture. In one embodiment, the conductive medium is a conductive gel or normal saline in a predetermined concentration (preferably about 15 mM~about 200 mM) and volume sufficient to provide a desired conductivity (>about 80 μS/cm). In some embodiments, the predetermined concentration is about 30 mM to about 200 mM, about 30 mM to about 150 mM, about 30 mM to about 120 mM, about 30 mM to about 100 mM, about 30 mM to about 200 mM, about 50 mM to about 200 mM, about 50 mM to about 150 mM, about 50 mM to about 100 mM, about 50 mM to about 100 mM, about 100 mM to about 200 mM, or about 150 mM to about 200 mM. In some embodiments, the desired conductivity is larger than about 80, about 90, about 100, about 120, about 150 or about 200 μS/cm.

In one embodiment, the packet has one or more fasteners on one side and one or more corresponding depressed elements on the opposite side so that the fasteners penetrate the depressed elements when the packet folds up. In one embodiment, there is an openable seal line between the two compartments. When the seal line is broken, the conductive medium would be absorbed by the liquid-absorbable pad to render it conductive.

In another aspect, the invention provides a transcranial electrostimulation apparatus, comprising:
  (i) a transcranial electrostimulator of the invention;
  (ii) one or more electrodes of the invention for detachable attachment to the scalp of a subject, the electrode(s) being driven by the transcranial burst electrostimulator; and
  (iii) a flexible head brace for adjustably securing the electrode(s) wherein the electrode(s) can be adjustably positioned anywhere on the head brace.

In one embodiment, the transcranial electrostimulation apparatus further comprises an ear warmer for placing accessories and wires of the system.

In another aspect, the invention provides a method applying a transcranial electrostimulation to a subject, comprising:
  (i) providing a transcranial electrostimulator of the invention comprising an alternating current source to provide direct current stimulation (tDCS) in combination with theta burst stimulation (TBS) as mentioned in the invention;
  (ii) sending a electrostimulation signal to electrodes of the invention; and
  (iii) transferring the electrostimulation signal from the electrodes to the subject.

The transcranial electro stimulation of the invention may facilitate enhanced functional recovery or development in patients experiencing neurologic dysfunction associated with stroke, TBI, learning and/or memory disorders, Alzheimer's disease, and/or other conditions. The transcranial electrostimulation of the invention may facilitate neurological consolidation of newly or recently acquired functional gains, learned skills, and/or memories, possibly through one or more mechanisms corresponding or related to LTP, depotentiation, LTD, and/or synaptic plasticity. Moreover, the transcranial electrostimulation of the invention may facilitate enhanced symptomatic relief associated with neurologic conditions involving maladaptive neuroplasticity, for example, tinnitus, auditory hallucinations, phantom limb pain or other chronic pain syndromes, and/or other conditions. Depending upon the nature of a particular condition, neural stimulation applied or delivered in accordance with several embodiments of the invention may affect neural firing likelihoods and/or influence, facilitate, and/or effectuate reorganization of interconnections or synapses between neurons to (a) provide at least some degree of functional recovery and/or functional gain; and/or (b) develop one or more compensatory mechanisms to at least partially overcome a functional deficit or shortcoming. Such reorganization of neural interconnections may be achieved, at least in part, by a change in the strength of synaptic connections through a process that corresponds to a mechanism commonly known as Long-Term Potentiation (LTP). Neural stimulation applied or delivered in accordance with certain embodiments of the invention may alternatively or additionally affect particular neural populations through a process that corresponds to a mechanism commonly known as Long-Term Depression (LTD). Neural stimulation delivered or applied to one or more target neural populations either alone or in conjunction or association with one or more behavioral activities and/or other types of adjunctive or synergistic therapies (e.g., a drug or chemical substance therapy, a neurotrophic or growth factor therapy, and/or a cell implantation therapy) may facilitate, effectuate, or enhance therapeutic efficacy, for example, through neural plasticity and the reorganization of synaptic interconnections between neurons.

As an example, a target neural population may comprise one or more portions of a patient's motor cortex. A neural location at which or a neural region in which stimulation signals are applied or delivered to or through a target neural population may be defined as a stimulation site. Thus, for a target neural population corresponding to the motor cortex, an exemplary stimulation site may comprise a location or region upon the patient's dura mater.

As another example, a target neural population may correspond to one or more portions of a patient's auditory cortex. A stimulation site may comprise an epidural or subdural cortical region that may facilitate the application, delivery, and/or transfer of stimulation signals to such a target neural population, for example, an epidural site adjacent or proximate to the Sylvian fissure. The application of unipolar stimulation signals to such a stimulation site in accordance with particular embodiments of the invention may increase the likelihood of affecting the target neural population in an intended manner.

A stimulation site may be identified in accordance with a variety of techniques, including (1) identification of one or more anatomical landmarks; (2) preoperatively (e.g., using Transcranial Stimulation) and/or intraoperatively stimulating one or more brain locations to identify or map particular neural regions that induce or evoke a given type of patient response (for example, a movement or a sensation); (3) estimating a location at which the brain may recruit neurons to carry out a given type of neural activity that was previously performed by a damaged portion of the brain; (4) an electrophysiologic signal measurement and/or analysis procedure (e.g., acquisition and/or analysis of EEG, EMG, MEG, coherence, partial coherence, and/or other signals); and/or (5) a neural imaging procedure. In general, the number and/or location of stimulation sites under consideration may depend upon the nature, number, and/or extent of a patient's neurological condition and/or functional deficits.

Various embodiments of the present invention may apply or deliver electrical stimulation at a subthreshold level or intensity, that is, at a level that raises or generally raises membrane potentials associated with a target neural population while avoiding the generation of a sufficient or statistically significant number of action potentials capable of triggering a neural function corresponding to the target neural population as a result of neural stimulation alone.

FIG. 1 is a schematic diagram of a system for applying transcranial electrostimulation to a stimulation site or region according to an embodiment of the invention. In various embodiments, the stimulation site may be upon, essentially upon, or proximate to the surface of the cortex of a subject S. The transcranial electrostimulation apparatus may comprise a transcranial electrostimulator 110 and a subject interface that includes a flexible head brace 130 for adjustably securing a set of electrodes, electrode arrangements and/or electrode assemblies 150 (hereinafter, "electrode set"). The electrode set can be adjusted and secured at the position of the head brace corresponding to the stimulation site to contact the scalp of the subject. In one embodiment, the electrode set 150 includes a first electrode 150a and a second electrode 150b. Various alternate embodiments may include additional electrode sets, which may be positioned or implanted at or proximate to a set of stimulation sites, or remote from one or more stimulation sites. Electrode sets can stimulate different neural or brain regions, e.g., regions carrying out different neural functions and/or regions carrying out neural functions at different locations of the body, including different extremities of the body.

The transcranial electrostimulator 110 generates and outputs stimulation signals, and the electrode set 150 facilitates application or delivery of the stimulation signals to the subject S. The transcranial electrostimulator 110 may perform, direct, and/or facilitate neural stimulation procedures in a manner that enhances efficacy and/or mitigates a likelihood of inducing collateral neural activity.

The transcranial electrostimulator 110 may comprise a direct current source and an alternating current source for providing direct current stimulation (tDCS) and theta burst stimulation (TBS). In the embodiment shown in FIG. 1, the transcranial electrostimulator 110 may comprise a direct current source 120 and an alternating current source 122. The transcranial electrostimulator 110 may further comprise a battery, an energy storage device, and/or power conversion circuitry (not shown in FIG. 1). The transcranial electrostimulator 110 may include a processor, a memory, and a programmable computer medium (not shown in FIG. 1). The transcranial electrostimulator 110 may be implemented as a computer or a microcontroller, and the programmable medium may comprise software, instructions, and/or configuration information loaded into the memory and/or hardware that performs, directs, and/or facilitates neural stimulation procedures in accordance with one or more methods of the present invention.

Figure 2:
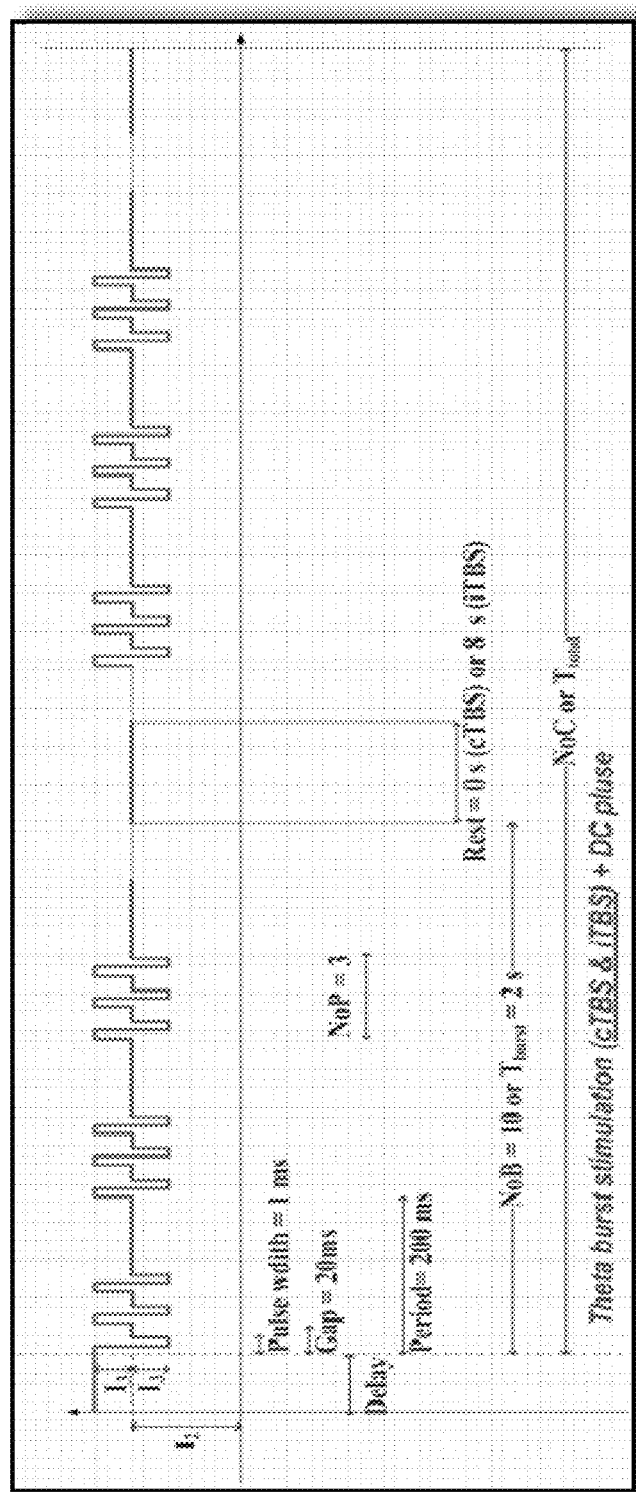
FIG. 2 is a graph illustrating parameters of a stimulation signal used in the system of FIG. 1 in accordance with one embodiment of the invention.

The direct current source 120 and an alternating current source 122 output stimulation signals. FIG. 2 is a graph illustrating parameters of a stimulation signal. The pulse system includes tDCS mode, cTBS mode and iTBS mode. In certain embodiments, the direct current source 120 may output a DC signal of 0 to ±5 mA. The alternating current source 122 may generate and/or output stimulation signals in accordance with a theta burst pattern. In one embodiment, the stimulation signal may be a symmetric or asymmetric biphasic waveform comprising a set or series of biphasic pulses, and which may be defined, characterized, or described by parameters shown below:

Direct current (DC): Adjustable DC current ($I_2$) 3 mA
Alternating Current (AC): Adjustable amplitude ($I_3$)±1.5 mA
Pulse width 1 ms,
Time Gap between every two consecutive pulses of a burst: 20 microseconds.
Burst Period: 200 microseconds.
Number of pulse (NoP) per burst: 3 pulses per burst.
Number of burst (NoB) per stimulation signal: 10 bursts per stimulation signal.
Rest time of cTBS mode: 0 seconds.
Rest time of iTBS mode: 8 seconds.
Delay time: 15 seconds.
Duration: 30 minutes.

Those skilled in the art will understand that pulse intensity or amplitude may decay during one or both pulse phases, and a pulse may be a charge-balanced waveform. Those skilled in the art will further understand that in an alternate embodiment, pulses can be biphasic.

Figure 3:
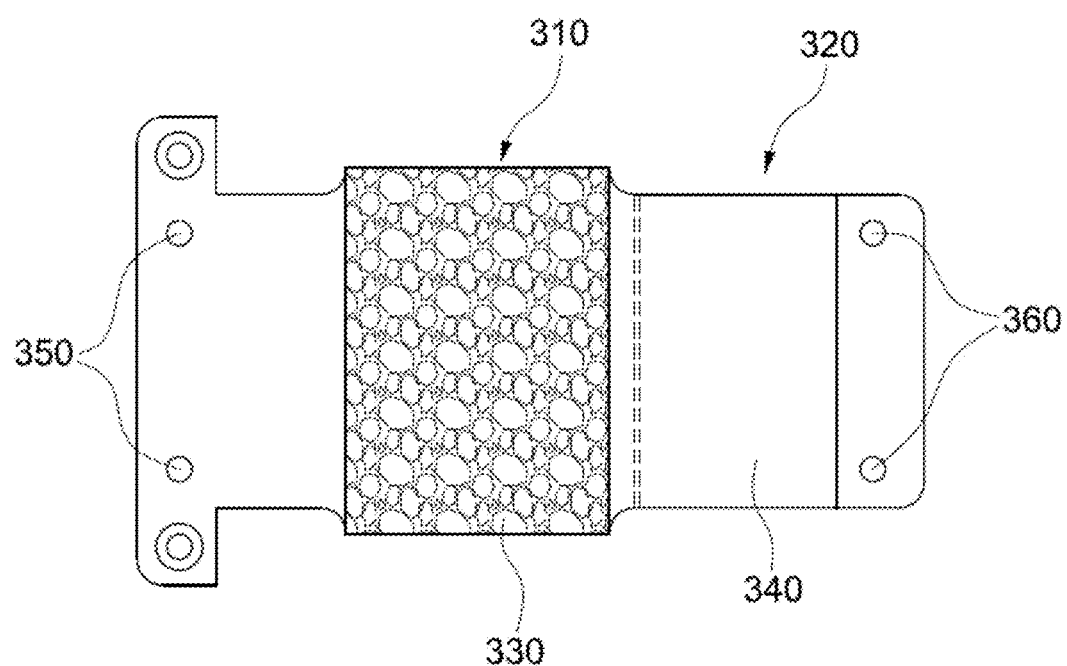
FIG. 3 depicts a disposable electrode in accordance with one embodiment of the invention.

The transcranial electrostimulator 110 may apply or output stimulation signals to electrode set 150 through a wire or wireless connection. The electrode is disposable and portable and the form thereof before use is illustrated in FIG. 3. The electrode 310 may comprise a plastic packet 320 having two compartments 330 and 340. One compartment contains a liquid-absorbable pad such as a sponge and the other compartment 340 contains a conductive medium such as normal saline in a predetermined concentration and volume sufficient to provide a desired conductivity. There are one or more fasteners 350 on one side of the packet and one or more corresponding depressed elements 360 located at the opposite side of the packet. Between the two compartments, there is an openable seal line 370. When the electrode is used, the openable seal line 370 is broken and the conductive medium would be absorbed by the liquid-absorbable pad to make it conductive.

Figure 4:
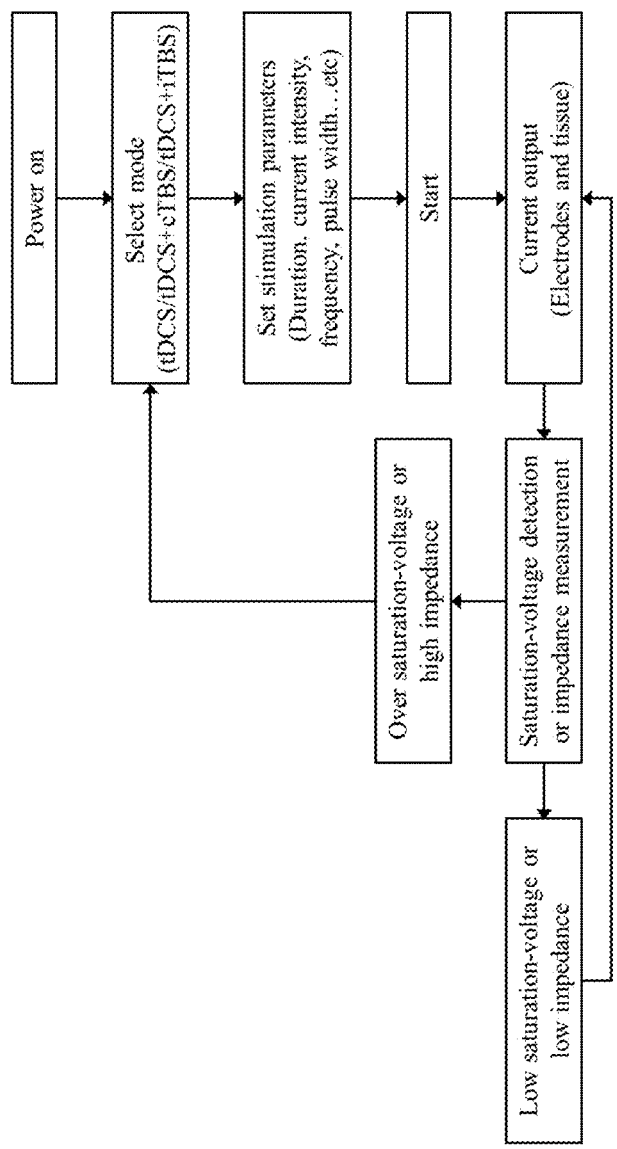
FIG. 4 is a flow chart illustrating a method for applying transcranial electrostimulation to a stimulation site in accordance with the present invention.

FIG. 4 is a flow chart illustrating a method for applying transcranial electrostimulation to a stimulation site in accordance with the present invention. FIG. 4, more specifically, illustrates a method 400 including a mode selection step 402, a parameters setting step 403, and an evaluation step 406.

The mode selection step 402 includes selecting and entering tDCS mode, cTBS mode and iTBS mode and their combinations depending on the proposed treatment regimen.

The parameters setting step 403 includes setting parameters for the selected mode, which may include establishing a direct current intensity, pulse current intensity and stimulation duration, etc.

Subsequent to the step 403, the electrical signal is transmitted to electrodes located at a stimulation site in step 404, where anodal unipolar stimulation and/or cathodal unipolar stimulation is applied to the patient, possibly in a manner that increases or enhances a likelihood or rate of patient functional recovery and/or development. The above application of the electrical signal may also involve the application of tDCS signals, cTBS signals, iTBS signals and any of their combinations during one or more time periods.

The evaluation step 406 may decide whether the stimulation has been of sufficient or adequate duration and/or effect. In particular embodiments, the evaluation step 406 may involve monitoring or measuring patient progress and/or functional capabilities through one or more standardized measures, tests, or tasks. For example, if an applied electrical signal of over saturation-voltage or high impedance is detected in step 407, the process would be directed back to step 402. If an applied electrical signal of low saturation-voltage or low impedance is detected in step 408, the process would be directed back to step 404.

From the foregoing, it will be appreciated that specific embodiments of the invention have been described herein for purposes of illustration, but that various modifications may be made without deviating from the spirit and scope of the invention. For example, aspects of the invention described in the context of particular embodiments can be combined or eliminated in other embodiments. Accordingly, the invention is not limited except as by the appended claims.

EXAMPLES

Example 1 Animal Studies of Transcranial Burst Electrostimulation of the Invention Male Wistar Rats were anesthetized by urethane and then fixed in 3-axe goniometer. Bregma of the rat was set as position 0 and the motor cortical areas in brain for upper and lower limbs of the rat were subjected to transcranial burst electrostimulation (Upper limb: AP: −1.5 mm, ML: 4.0 mm; Lower limb: AP: 1.0 mm, ML: 1.25 mm). Simultaneously, the electrical signal in brachioradialis muscle of upper limb was recorded to measure motor evoked potential (MEP) in motor cortical areas in brain receiving electrostimulation. The change of brain plasticity can be determined by MEP to evaluate whether there is a long-term potentiation (LTP)-like plasticity or long-term depression (LTD)-like plasticity. The fact that MEP maintains, increases or decreases for a period of time shows that the brain or neuronal plasticity can be changed.

Figure 5:
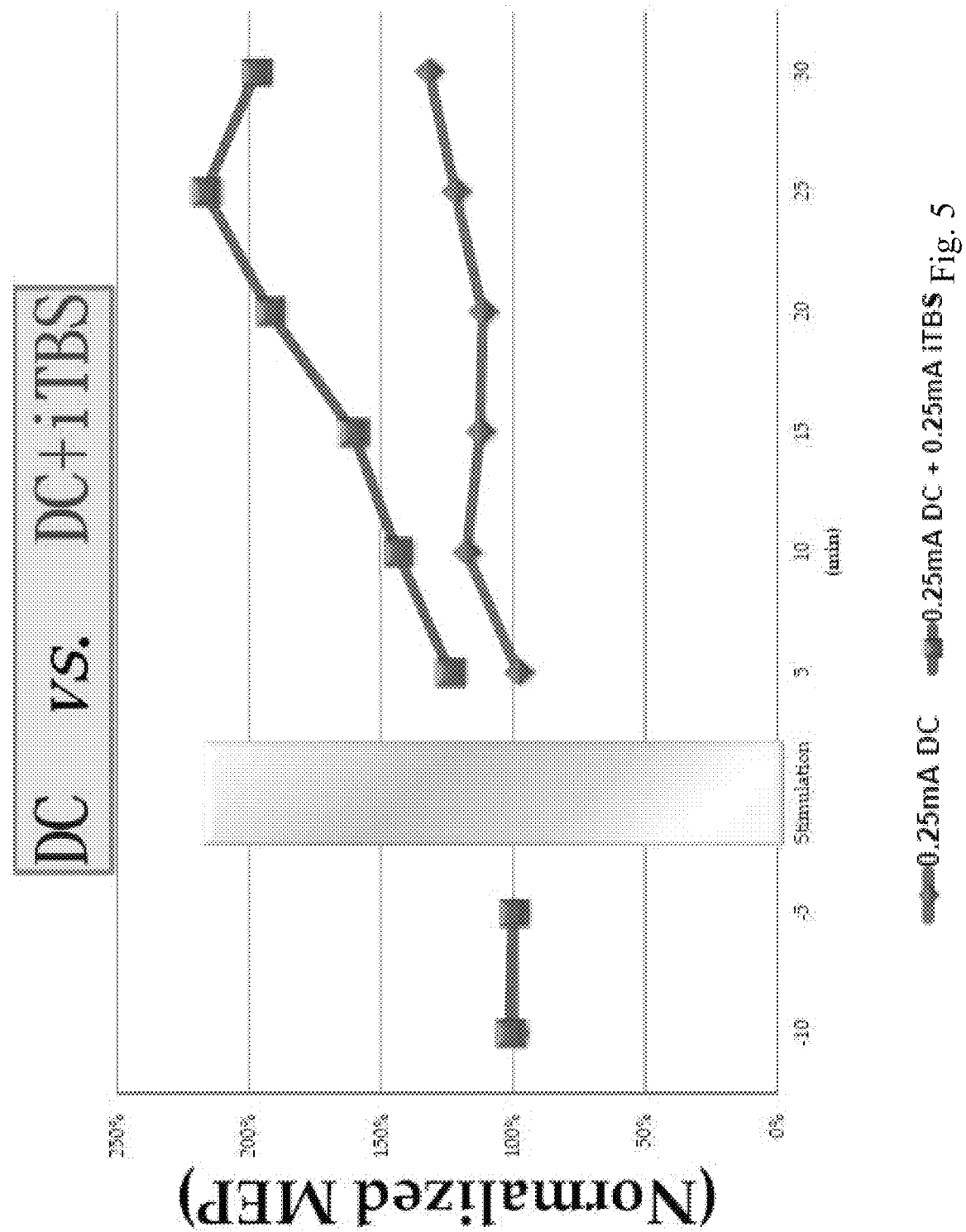
FIG. 5 shows the effects of waveforms in an animal study.

The study used 15 rats subjected to the electrostimulation according to the method illustrated in FIG. 4, wherein the parameters for providing stimulation signal are described in paragraph [0046]. FIG. 5 shows the effects of waveforms in the animal study. The effect of the electrostimulation protocol (i.e., DC, and DC combined with iTBS) on the MEP size in anesthetized rats was investigated. The effect of electrostimulation on MEP amplitude was tested in 5-min intervals; twice before electrostimulation as the baseline condition (for a total of 10 min), and 6 times after electrostimulation (for a total of 30 min). FIG. 5 shows the time course MEP changes before and after DC and DC combined with iTBS protocols. No significant difference was found in MEP responses before electrostimulation. However, the results in the DC combined with iTBS group always exhibited a larger MEP amplitude than the pure DC group did under any stimulation intensities. The results demonstrate that the DC combined with iTBS waveform exhibited a better neuroplastic effect than the DC waveform did.

Figure 6:
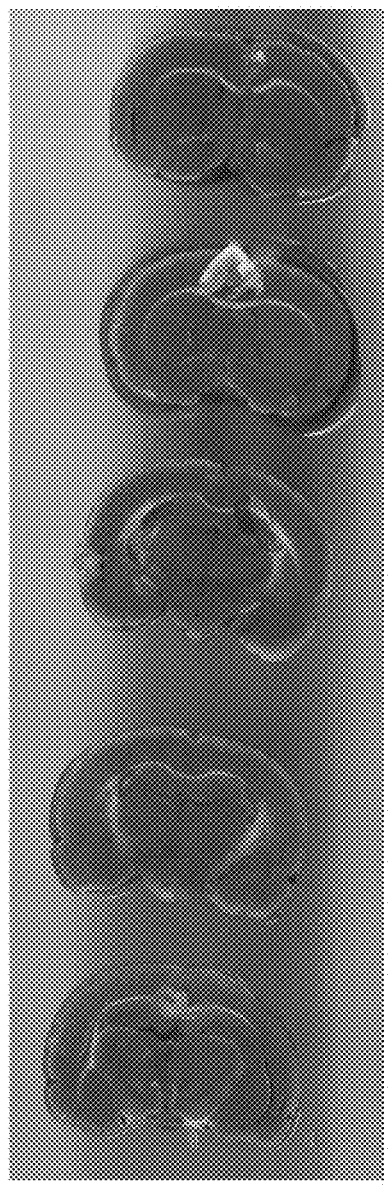
FIG. 6 shows experimental results of the brain tissues subjected to the transcranial electrostimulation of the invention.

The transcranial burst electrostimulation of the invention (tDCS+iTBS model) was further evaluated for safety. Six rats were anesthetized and then given transcranial electrostimulation with 0.1 A/m$^2$, 0.4 A/m$^2$ and 0.8 A/m$^2$ current density for 30 minutes. The results showed no significant scalp burns. The skins were further removed and subjected to H & E staining, and the results show no skin burns. The brain tissue of the rats was taken to check for damage. The brain tissue was sectioned and stained with 2% 2,3,5-triphenyltetrazolium chloride (TCC). The LDH in mitochondria of brain tissue can reduce TCC and the reduced TCC exhibits a dark red color. If cells are dead or damaged, LDH cannot perform the function of reducing TCC, and TCC remains white. After staining, the brain tissues were fixed with 4% paraformaldehyde and then subjected to image analysis to calculate the volume of damaged tissue. As shown in FIG. 6, no damage was found in the brain tissues.

Example 2 Clinical Study

Twenty-four stroke patients were enrolled in a clinical study. The patients were divided into two groups, a control group and an experiment group. The control patients received functional electrical stimulation (FES) cycling training, while the experimental patients received the transcranial burst electrostimulation of the invention and FES-cycling training. MOTOmed Viva 2 (Medimotion Ltd.) was used in the FES-cycling training. One positive electrode of the transcranial burst electrostimulation system of the invention was placed on the motor cortical area (M1) of the head and the other negative electrode was placed on the back of the neck. The patients received tDCS treatment for 30 minutes each time. The output current was 0-2.0 mA and the corresponding current density was 0-0.08 mA/cm$^2$.

After four weeks of treatment, the following evaluations were performed to evaluate the effect of the treatment: kinetic movement of FES-cycling training, modified Ashworth scale (MAS) (Bohannon, R. and Smith, M. (1987), "Interrater reliability of a modified Ashworth scale of muscle spasticity." Physical Therapy 67(2): 206) and gait analysis (Sutherland, D H. (2002). The evolution of clinical gait analysis: Part II Kinematics Gait & Posture. 16: 159-179). Furthermore, functional Near-Infrared Spectroscopy (fNIR or fNIRS) was used to measure functional neuroimaging. NIR spectrum light has the advantage of occupying the optical window in which skin, tissue, and bone are mostly transparent, in the spectrum of 700-900 nm, while hemoglobin (Hb) and deoxygenated-hemoglobin (deoxy-Hb) are stronger absorbers of light. Differences in the absorption spectra of deoxy-Hb and oxy-Hb allow measurement of relative changes in hemoglobin concentration through the use of light attenuation at multiple wavelengths (Villringer, A. et al., "*Near infrared spectroscopy (NIRS): A new tool to study hemodynamic changes during activation of brain function in human adults*". Neuroscience Letters 154 (1-2): 101-104). Wavelengths of 830 nm and 760 nm were selected for the measurement.

What is claimed is:

1. A transcranial electrostimulator, comprising:
  a first current source providing a direct current stimulation, and
  a second current source providing an alternating current stimulation;
  wherein the direct current stimulation is delivered with an adjustable direct current in a range of about 0 to +/−about 5 mA, the alternating current stimulation is delivered with an alternating current having a theta burst pattern with amplitude ranging from 0 to +/−5 mA and multiple bursts each having 2 to 5 pulses, each pulse having a pulse width of about 0.1 to about 3 ms, a gap between two adjacent pulses is about 5 ms to 30 ms, and the burst is repeating every 150 ms to 500 ms, wherein the bursts are continuous to provide a continuous theta burst pattern or intermittent to provide an intermittent theta burst pattern, and the direct current stimulation and the alternating current stimulation are superimposed into a single current stimulation signal.

2. The transcranial electrostimulator of claim 1, wherein the multiple bursts of the alternating current stimulation include 2 to 30 bursts per stimulation.

3. The transcranial electrostimulator of claim 1, wherein each burst has 3 pulses.

4. The transcranial electrostimulator of claim 1, wherein the gap is about 20 ms.

5. The transcranial electrostimulator of claim 1, wherein the pulse is repeated about every 200 ms.

6. The transcranial electro stimulator of claim 1, wherein an intermittent period between bursts of the intermittent theta burst pattern is about 2 seconds to about 30 seconds.

7. The transcranial electro stimulator of claim 1, wherein an intermittent period between bursts of the intermittent theta burst pattern is about 8 seconds.

8. The transcranial electrostimulator of claim 1, wherein the alternating current stimulation is delivered for 0 to 30 minutes.

9. The transcranial electrostimulator of claim 1, wherein the continuous theta burst pattern or intermittent theta burst pattern can optionally include a time delay between bursts.

10. The transcranial electrostimulator of claim 9, wherein the time delay is about 0 seconds to 15 seconds.

11. A transcranial electrostimulation apparatus, comprising:
(i) a transcranial electrostimulator of claim 1;
(ii) one or more electrodes for detachable attachment to the scalp of a subject, the electrode(s) being driven by the transcranial electrostimulator; and
(iii) a flexible head brace for adjustably securing the electrode(s) wherein the electrode(s) can be adjustably positioned anywhere on the head brace.

12. The transcranial electrostimulation apparatus of claim 11, wherein the transcranial electrostimulation apparatus further comprises an ear warmer for placing accessories and wires of the apparatus.

13. A method applying a transcranial electrostimulation to a subject, comprising:
(i) providing a transcranial electrostimulator of claim 1;
(ii) sending a electrostimulation signal from the transcranial electrostimulator to electrodes electrically connected to the subject; and
(iii) transferring the electrostimulation signal from the electrodes to the subject.

* * * * *